United States Patent [19]

Goldstone et al.

[11] Patent Number: 5,024,228
[45] Date of Patent: Jun. 18, 1991

[54] ELECTRODE ENDOTRACHEAL TUBE

[76] Inventors: Andrew C. Goldstone, 4000 N. Charles St., Apt. 511, Baltimore, Md. 21218; Raymond L. Schettino, 8402 Chapel Hill Ct., Baltimore, Md. 21237

[21] Appl. No.: 442,901

[22] Filed: Nov. 29, 1989

[51] Int. Cl.$^5$ .......................................... A61B 5/0488
[52] U.S. Cl. .................................... 128/642; 128/733
[58] Field of Search ............................... 128/642, 733

[56] References Cited

U.S. PATENT DOCUMENTS 4,155,353  5/1979  Rea et al. ............................ 128/642
4,198,963  4/1980  Barkalow et al. ............... 128/642 X

OTHER PUBLICATIONS

Mylrea, Kenneth C., et al., "ECG Lead with the Endotracheal Tube", Critical Care Medicine, vol. II, No. 3, Mar., 1983.
Rao, A. J., et al., "Model of a New Generation of Tracheaostomy and Endotracheal Tubes", Ann Otol Rhinol Laryngol, 98: 1989, pp. 157-159.
Nicolet Nerve Integrity Monitor-User's Guide, Mar., 1988, Nicolet Biomedical Instruments, Madison, Wisconsin.
Engel, P. M., et al., "A Device for the Location and Protection of the Recurrent Laryngeal Nerve During Operations Upon the Neck", Surgery, Gynecology and Obstetrics, 152: 824-826, 1981.
Lipton, R. J., et al., "Intraoperative Electrophysiologic Monitoring of Laryngeal Muscle During Thyroid Surgery", Laryngoscope, 98: 1291-1296, 1988.
Fujita, M. et al., "A New Surface Electrode for Recording from the Posterior Cricoarytenoid Muscle", Laryngoscope, 99: 316-320, 1989.
Spahn, J. G., et al., "Identification of the Motor Laryngeal Nerves—A New Electrical Stimulation Technique", Laryngoscope, 91: 1865-1868, Nov., 1981.
Hvidegaard, T., et al., "Endolaryngeal Devices for Perioperative Identification and Functional Testing of the Recurrent Nerve", Otolaryngology—Head and Neck Surgery, 92(3): 292-294, Jun., 1984.
Woltering, E., et al., "A Method for Intraoperative Identification of the Recurrent Laryngeal Nerve", The American Journal of Surgery, 148: 438-440, Oct. 1984.
Zini, C., et al., "Facial-Nerve and Vocal-Cord Monitoring During Otoneurosurgical Operations", Arch Otolaryngol Head Neck Surgery, 113: 1291-1293.
Davis, W. E., et al., "Recurrent Laryngeal Nerve Localization Using a Microlaryngeal Electrode", Otolaryngol Head and Neck Surgery, 87: 330-333, May-Jun. 1979.
Payne, J. K., et al., "A Surface Electrode for Laryngeal Electromyography", Journal of Neurology, Neuorsurgery, and Psyciatry, 43: 853-854, 1980.
Satoh, I., et al., "Evoked Electromyographic Test Applied for Recurrent Laryngeal Nerve Paralysis", The Laryngoscope, 88: 2022-2031, 1978.
Shedd, D. P., et al., "Identification of the Recurrent Laryngeal Nerve", Arch Surg., 92: 861-864, Jun., 1966.
Johns, M. E., et al., "Complications in Otolaryngology—Head and Neck Surgery", Chapter 18, pp. 175-180, 1986, Toronto.
"The EMG Electrode Endotracheal Tube: A New Surface Electrode for Monitoring Recurrent Laryngeal Nerve-Vocal Cord Muscle Integrity in the Intubated Patient", Goldstone, Andrew C. and Schettino, Raymond A., Aug. 25, 1989.

Primary Examiner—Lee S. Cohen
Attorney, Agent, or Firm—Marshall, O'Toole, Gerstein, Murray & Bicknell

[57] ABSTRACT

An electrode endotracheal tube for detecting electromyographic signals in the laryngeal muscles and comprising electrode wires running in a direction parallel to the central axis of the endotracheal tube. Each wire is insulated from electrical contact along a first portion of its length and is exposed along a second portion. The exposed portion is at a location on the tube which permits the exposed portion to contact the adjacent laryngeal muscles when the endotracheal tube is inserted into the trachea.

7 Claims, 4 Drawing Sheets

ELECTRODE ENDOTRACHEAL TUBE

BACKGROUND OF THE INVENTION

The present invention relates generally to electrodes for detecting electromyographic (EMG) signals of the laryngeal muscles, and more particularly to electrodes which are mounted on an endotracheal tube.

The recurrent laryngeal nerves, hereinafter referred to as the laryngeal nerves, course through the neck to the intrinsic laryngeal muscles, hereinafter referred to as the laryngeal muscles. There are two laryngeal nerves, one on the left side and one on the right of the neck. Each nerve controls a set of laryngeal muscles, including a vocal cord.

Damage to laryngeal nerves is a common complication of neck surgery. When the anatomy is relatively normal, the course of a laryngeal nerve along the neck is usually discernible. However, the presence of abnormal tissue, such as tumor, inflammation or trauma may make anatomic dissection of the nerve without damage nearly impossible.

If a laryngeal nerve is damaged during surgery, paralysis of the related laryngeal muscles can occur. Paralysis of the laryngeal muscles results in loss of speech and may also disrupt breathing by preventing air passage through the trachea. There is, therefore, a need for an apparatus which will aid in the location of the laryngeal nerves. It is also desirable to have an apparatus which warns a surgeon when contact is made with a laryngeal nerve.

During surgery a tube is usually placed through the patient's nose or mouth and into the trachea, passing between the sets of laryngeal muscles. This endotracheal tube is used to ventilate the lungs and may also be used to provide anesthesia. Most endotracheal tubes include an inflatable cuff surrounding the tube. Once the tube is inserted into the trachea, the cuff is inflated to prevent air from escaping by passing between the tube and the trachea wall.

One prior art method of locating a laryngeal nerve uses an endotracheal tube having an additional cuff located to be adjacent both sets of laryngeal muscles when the tube is placed in the trachea. See, e.g. Engel P.M., et al. "A Device For The Location and Protection of the Recurrent Laryngeal Nerve During Operations Upon the Neck." *Surgery, Gynecology, and Obstetrics*, 152:824–826, 1981. The additional cuff is inflated and connected to a device for detecting pressure changes. A probe delivering an electric charge is used to stimulate the laryngeal nerve. When the probe contacts the nerve, the related set of laryngeal muscles contract causing a pressure change within the cuff, which can be detected by the pressure sensing device. Thus a surgeon can locate a laryngeal nerve by using the probe to stimulate various portions of the neck until a response is noted on the pressure sensing device.

The pressure sensitive device, however, does not operate satisfactorily. It can only detect relatively large movements of the laryngeal muscles. Thus it may not be sensitive enough to register all responses in the muscles when the nerve is electrically stimulated.

The pressure sensitive device also may be unable to detect the indigenous electric discharge which occurs when a laryngeal nerve is manipulated. Laryngeal nerves emit an electrical impulse which travels to the related set of laryngeal muscles when the nerve is manipulated or is contacted by a surgical instrument. The impulse from contact or manipulation is generally smaller than that which can occur by use of outside electrical stimulation. Thus the pressure sensitive device may not be able to warn a surgeon when damage to a laryngeal nerve is imminent due to contact with a surgical instrument.

Another method of locating a laryngeal nerve is the use of electrodes emplaced directly into a related laryngeal muscle. See, e.g., Lipton R.J. et al., "Intraoperative Electrophysiologic Monitoring of Laryngeal Muscle During Thyroid Surgery." *Laryngoscope*, 98:1292–1296, 1988. These electrodes are connected to an EMG machine which measures changes in voltage in the muscle. A number of different electrode types are known in the art, including needles, needle pairs and hooked wires. These devices are capable of detecting electrical changes in a laryngeal muscle caused by external electrical stimulation of the related laryngeal nerve. These devices are also sensitive enough to detect the electrical changes which occur in a muscle when the related laryngeal nerve is stimulated by manipulation, and, thus can be used to inform a surgeon when contact is made with a laryngeal nerve. These devices are undesirable, however, because they are difficult to accurately emplace in the muscle. A medical technique requiring a high degree of expertise must be mastered by a surgeon before these electrodes can be used.

Another device for measuring EMG activity in the laryngeal muscles comprises a tube substantially thinner than an endotracheal tube, and containing electrode wires which extend from the tube's interior through the tube wall and then circumferentially around the tube. The tube is placed into the esophagus, which is located just behind the trachea. This tube monitors the posterior laryngeal muscles, the muscles at the back of the trachea, through the front or anterior esophagus wall. See e.g., Fujita et al., "A New Surface Electrode for Recording from the Posterior Cricoarytenoid Muscle". *Laryngoscope*, 99:316–320, 1989. The circumferential electrode device is designed for use while the patient is awake, to measure EMG activity during normal breathing and speaking, although it could also be used during surgery.

The circumferential electrode device is inadequate for use in locating and protecting the laryngeal nerve for a number of reasons. First, because each set of laryngeal muscles is located adjacent a respective right or left side of the trachea, the circumferential electrode device allows measurement of EMG signals from only one of the two sets of laryngeal muscles. More particularly, the device is thin and must be placed against either the right or left side of the anterior esophagus wall. Since the device contacts only one side of the anterior wall, it can only monitor the set of laryngeal muscles in the trachea closer to that one side. Second, placement of the thin tube is difficult because it requires that the thin tube be positioned in the esophagus without any direct visualization. Additionally, a circumferential electrode configuration could not be used on an endotracheal tube employed for ventilation during surgery, because that kind of tube is relatively thick; and a given electrode surrounding the thick endotracheal tube would unavoidably be in contact with both sets of laryngeal muscles at the same time.

SUMMARY OF THE INVENTION

There is provided in accordance with the present invention an endotracheal tube which performs the functions of ventilating the lungs during surgery and monitoring the EMG signals of the laryngeal muscles. The endotracheal tube comprises a flexible tube having a distal end and a proximal end. The tube contains a main lumen for ventilating the lungs, an inflatable cuff and a thin lumen for inflating the cuff. The thin lumen is located in the wall of the tube and is attached to a fitting for connecting the thin lumen to an air source for inflating the cuff.

The tube contains one or more electrode wires which run in a direction parallel to the central axis of the tube. Each electrode wire is insulated against electrical contact at a first wire portion located between the ends of the tube. Insulation may be achieved by embedding the first wire portion within the wall of the endotracheal tube. An uninsulated second wire portion, located between the tube's distal end and the first wire portion, lies exposed on the surface of the endotracheal tube permitting electrical contact to be made by the second wire portion.

When an endotracheal tube is inserted in a human patient, the distal end of the tube must be located above the point where the trachea splits to communicate with both lungs, thus insuring that both lungs are ventilated. The tube must be inserted far enough into the trachea, however, so that the cuff is located below the laryngeal muscles. The cuff must also be located low enough so that when it is inflated it does not push against the laryngeal nerves which run up the neck, near the upper portion of the trachea, toward the laryngeal muscles. Pressure by the cuff could damage the laryngeal nerves. When the distal end of the endotracheal tube is above the split in the trachea and the cuff is below the location of the laryngeal muscles, the tube is properly positioned.

The second or uninsulated portion of each electrode wire is positioned on the tube so that the uninsulated portion contacts a set of laryngeal muscles, particularly a vocal cord of that set, when the endotracheal tube is properly positioned. The uninsulated wire portion must be long enough so that contact with the laryngeal muscles can be easily accomplished. The uninsulated portion must not, however, be so long that it contacts parts of the patient's anatomy other than the laryngeal muscles. Contact with other parts of the patient's anatomy, such as the tongue or the pharyngeal muscles, could cause the electrode wire to receive EMG signals from sources other than the laryngeal muscles. A given length and location on the tube of the second wire portion will suffice for virtually all adults. However, the length and location of the second wire portion may differ for an electrode endotracheal tube intended for use in children or individuals who have other than the normal sized anatomy usually found in adults.

The electrodes are capable of detecting EMG signals of two distinct types. The first type of signal is one produced when a laryngeal nerve is stimulated by an electric probe. When a voltage is applied on or near a laryngeal nerve, the electrical pulse is carried to the related set of laryngeal muscles through the nerve. The electrode endotracheal tube can detect that electric pulse when it is transferred into the related laryngeal muscles. Thus a surgeon can locate a nerve by electrically stimulating various portions of the neck during surgery and noting whether a response is detected by the electrode wire contacting the related laryngeal muscles.

The second type of EMG signal which the electrode endotracheal tube will be able to detect is one caused by physical manipulation of a laryngeal nerve. When laryngeal nerve tissue is manipulated or contacted by a surgical instrument, the nerve emits an electrical pulse. That pulse is carried to the related laryngeal muscles via the nerve. Thus, when a surgeon manipulates or contacts a laryngeal nerve, an EMG signal can be detected in the related laryngeal muscles. In this way the invention can be used to alert a surgeon when potentially damaging contact with a laryngeal nerve is imminent.

Located near the proximal end of the tube are conventional mechanisms for connecting the electrode wires to a device for processing EMG signals.

The electrode endotracheal tube also has the advantage of being able to alert doctors when the endotracheal tube is either too proximal or too distal in the trachea to allow proper ventilation. When the patient is under a light level of anesthesia, EMG signals associated with breathing can be detected in the laryngeal muscles. If those signals are not detected when the patient is initially intubated, i.e. when the endotracheal tube is inserted, it is an indication that the tube is not properly placed.

The present invention also has the advantage of being easy to accurately place. Endotracheal tubes have been used in surgery for many years, and many doctors, particularly anesthesiologists, are already skilled in the insertion of those tubes. Thus there is already a large group of medical professionals who can properly place the electrode endotracheal tube.

Other features and advantages are inherent in the electrode endotracheal tube claimed and disclosed or will become apparent to those skilled in the art from the following detailed description in conjunction with the accompanying diagrammatic drawings.

DETAILED DESCRIPTION OF THE INVENTION

Figure 1:
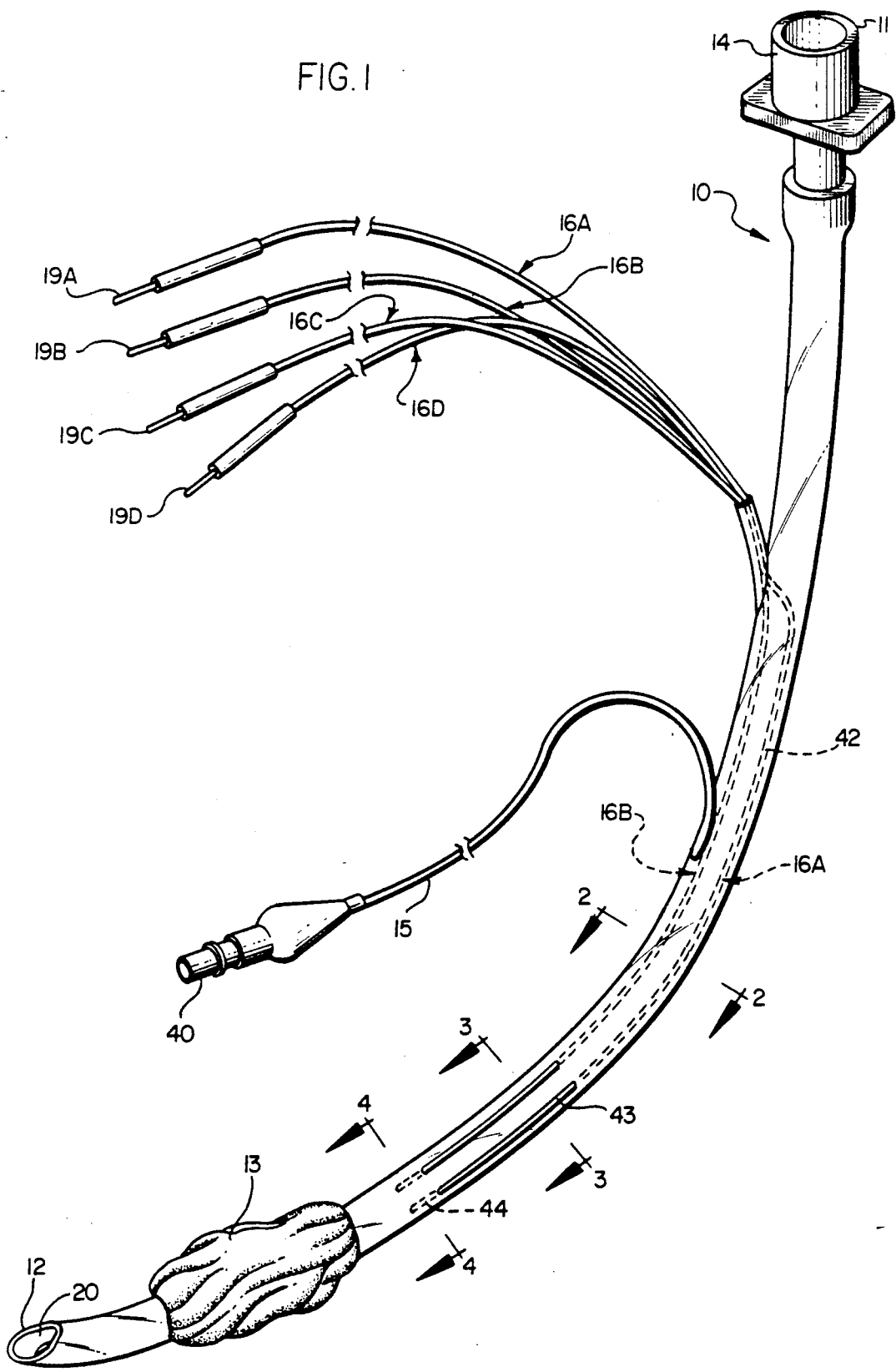
FIG. 1 is a perspective of an embodiment of an electrode endotracheal tube constructed in accordance with the present invention.

Referring initially to FIGS. 1-4, indicated generally at 10, is an electrode endotracheal tube constructed in accordance with an embodiment of the present invention and comprising a flexible, non-electrically conducting tube having a proximal end 11 and a distal end 12.

Tube 10 has a main lumen 20 for transporting gases to and from the lungs.

At proximal end 11 is a fitting 14 for connecting tube 10 to a respirating machine (not shown) which injects and withdraws air from the lungs. A cuff 13 is located near distal end 12. Cuff 13 is shown in an uninflated condition in FIG. 1 and can be inflated by use of a cuff inflating conduit 15, which is attached to a source of compressed air (not shown) by a fitting 40. Cuff inflating conduit 15 communicates with a lumen 25 located in the wall 24 of tube 10 (FIGS. 2-4), and lumen 25, in turn, communicates with cuff 13. Wall 24 is defined by inner surface 22 and outer surface 23.

Associated with tube 10 are four electrode wires indicated generally at 16A, 16B, 16C and 16D, each composed of an electrically conducting material and each running from a location between the two tube ends 11 and 12 toward distal end 12. The term "wires" includes any type of electrically conducting lead suitable for use as an electrode, including metal paint, metallic tape or metal strips. Wires 16A-D run in a direction parallel to the tube's central axis 21. Each electrode wire has a first portion 42, located between proximal end 11 and distal end 12, and insulated against electrical contact. In the embodiment of the invention depicted in FIGS. 1-4, each first wire portion 42 is embedded within tube wall 24 to insulate wire portion 42 from electrical contact.

A second wire portion 43 is located between distal end 12 and first wire portion 42, on outer surface 23 of tube 10. Each second wire portion 43 is uninsulated and capable of forming an electrical contact. Each wire may have an optional third portion 44 embedded within wall 24 between distal end 12 and second wire portion 43. Each wire is embedded at third portion 44 to keep second portion 43 in place on outer tube surface 23. Other expedients can be used to insure that second portion 43 remains in place, so long as those other expedients permit electrical contact between second portion 43 and adjacent laryngeal muscles.

In a preferred embodiment of electrode endotracheal tube 10, second wire portion 43 begins 10 cm from distal end 12 and ends 3 cm closer to proximal end 11. In other embodiments of electrode endotracheal tube 10, second wire portion 43 may begin 8 to 12 cm from distal end 12 and end 2 to 4 cm closer to proximal end 11.

Figure 2:
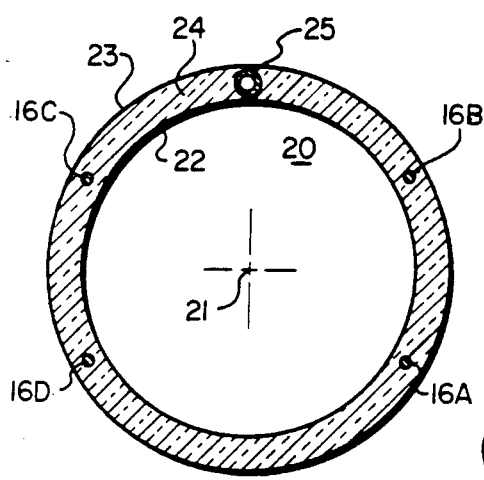
FIG. 2 is a sectional view taken along line 2—2 in FIG. 1.
Figure 3:
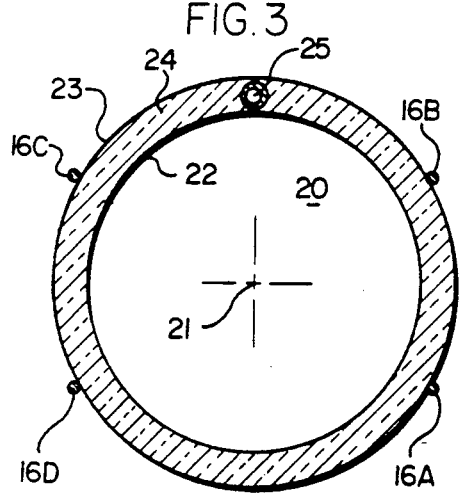
FIG. 3 is a sectional view taken along line 3—3 in FIG. 1.
Figure 4:
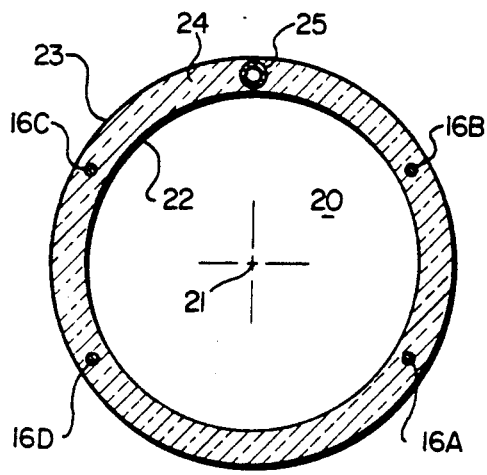
FIG. 4 is a sectional view taken along line 4—4 in FIG. 1.

As best shown in FIGS. 2-4, wires 16A-D run in pairs, two along the tube's left side, e.g. 16A and 16B, and two along the tube's right side, e.g. 16C and 16D. When an electrode pair is used to monitor the EMG activity in any muscle, those electrodes are called a bipolar electrode pair. It is possible to use single or monopolar electrodes to monitor muscles, however, the use of a bipolar electrode provides greater accuracy. The workings of electrodes and the advantages of bipolar over monopolar electrodes are well known to one skilled in the art.

Electrical connecting plugs 19A, 19B, 19C and 19D are used to connect wires 16A-D to an EMG processing machine (not shown). Any means capable of forming electrical contact such as ports, alligator clips or insulated wires with bared ends could be used with the present invention instead of the depicted plugs.

Figure 5:
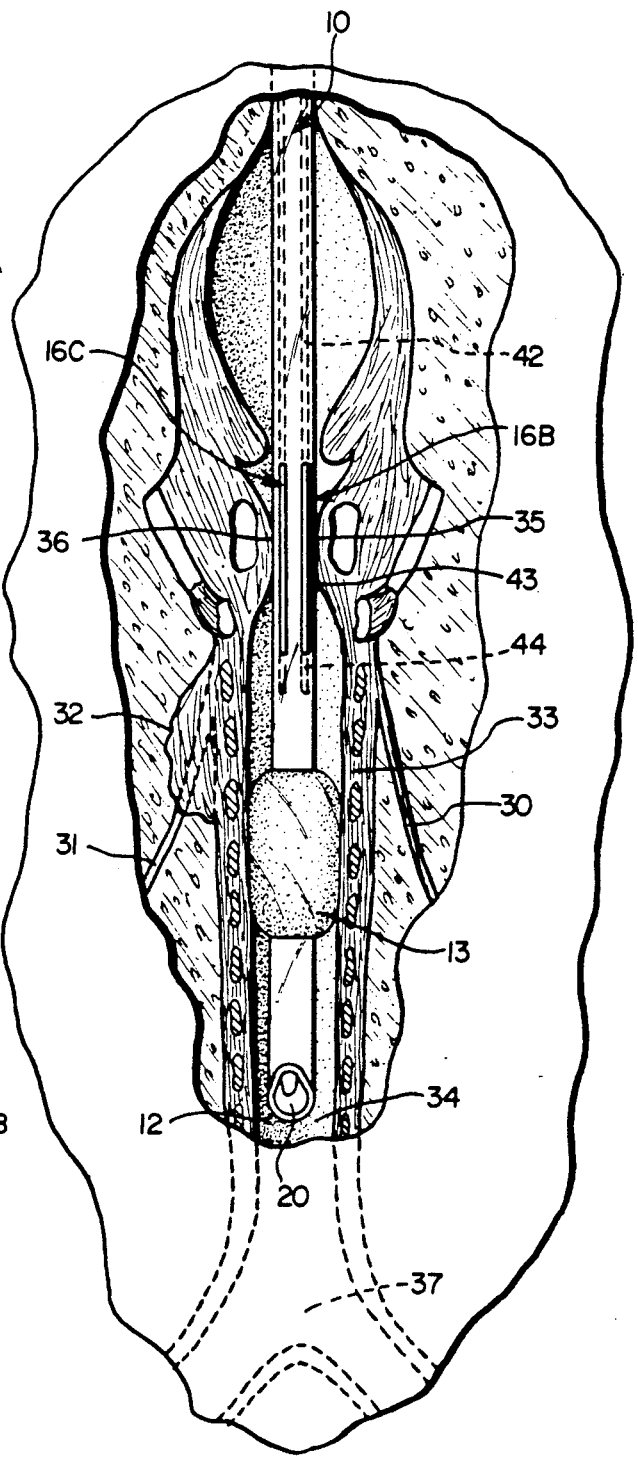
FIG. 5 is a fragmentary, vertical sectional view of the neck and chest region of a human body showing the placement of the electrode endotracheal tube.

FIG. 5 shows electrode endotracheal tube 10 properly inserted into the trachea of a patient. Tube 10 is inserted between a set of left laryngeal muscles 35 and a set of right laryngeal muscles 36 and into the trachea 34. Distal end 12 is located within trachea 34 above the junction 37 where the trachea splits into two passages, each going to a separate lung. Cuff 13 is located below laryngeal muscles 35 and 36. Second wire portions 43 are in contact with laryngeal muscles 35 and 36. Wires 16A and 16B are in contact with left laryngeal muscles 35 and wires 16C and 16D are in contact with right laryngeal muscles 36. The right recurrent laryngeal nerve 31 is shown located beneath the thyroid 32. The left recurrent laryngeal nerve 30 is exposed, as depicted. Cuff 13 is shown inflated to prevent air from escaping between the wall 33 of trachea 34 and tube 10.

Figure 6:
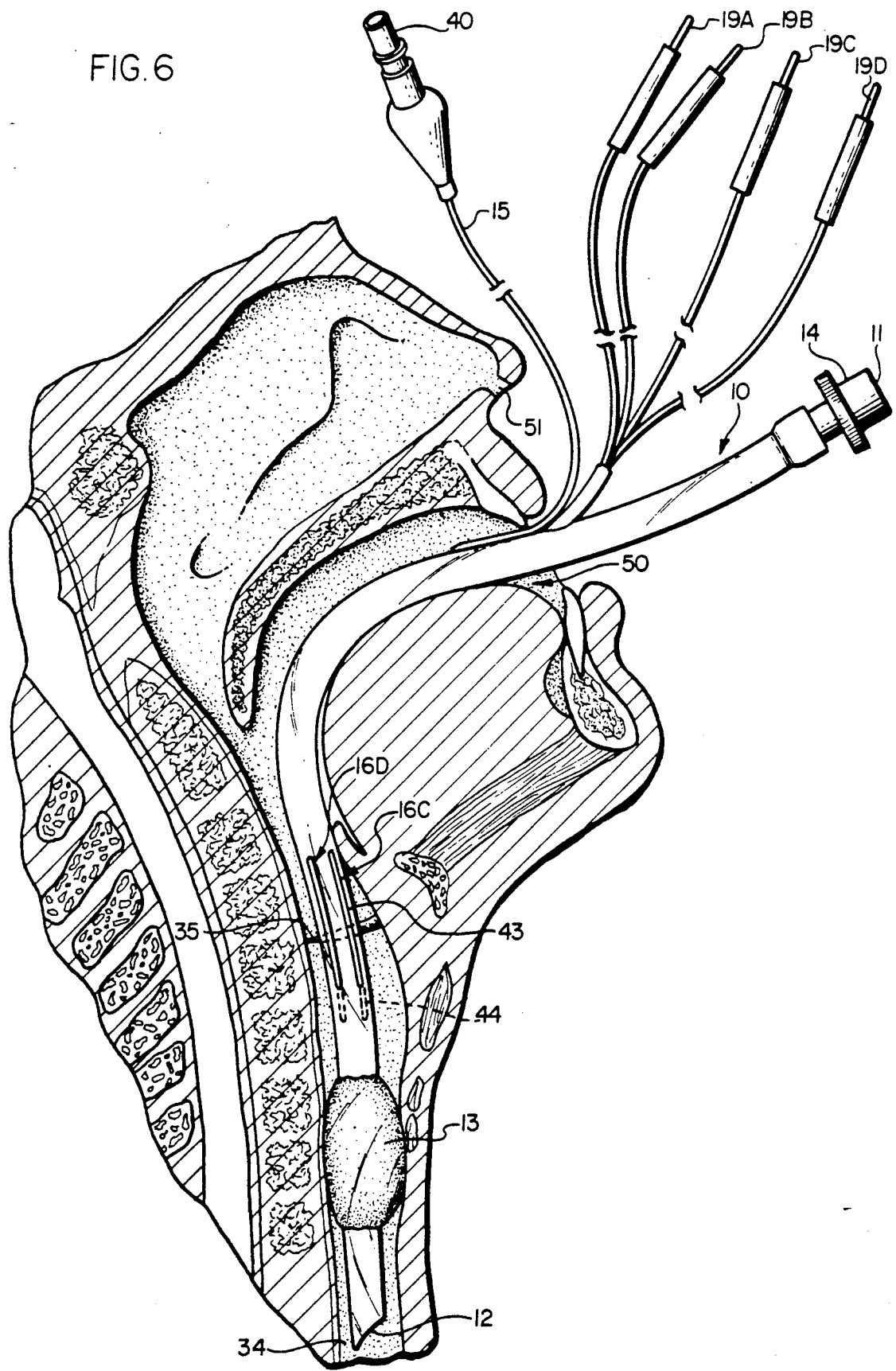
FIG. 6 is a fragmentary, sectional view of the head and neck region showing the placement of the electrode endotracheal tube.

FIG. 6 shows tube 10 inserted orally through mouth 50 and passing into trachea 34. Another embodiment of the present invention would use a slightly thinner endotracheal tube which could be inserted nasally through a nostril 51 and into trachea 34.

Figure 7:
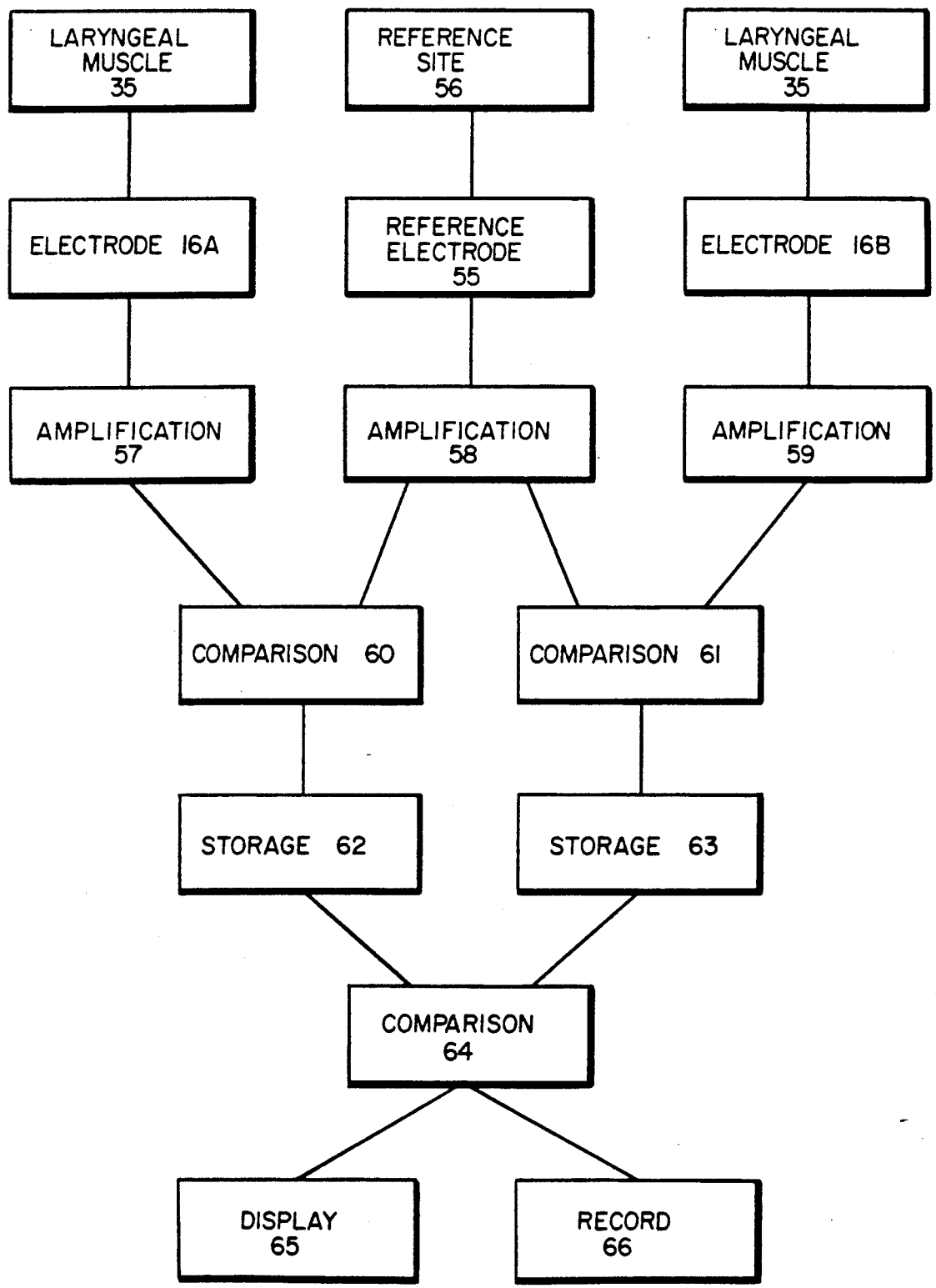
FIG. 7 is a schematic diagram showing the steps employed in processing an EMG signal from an electrode.

FIG. 7 is a schematic diagram showing the steps that could be used in processing EMG signals from an embodiment of electrode endotracheal tube having a bipolar electrode pair. The electrode endotracheal tube 10 could be used to provide a variety of information. The processing steps described below constitute only one way of using the information detected by the electrode endotracheal tube.

Each electrode is connected to a conventional, commercially available EMG processing machine such as the Nicolet Nerve Integrity Monitor-2 as described in the *Nicolet Nerve Integrity Monitor-2 User's Guide*, March, 1988, Nicolet Biomedical Instruments, Madison, Wis., and the disclosure therein is incorporated herein by reference. A device of this type can process the EMG signals and provide information to the surgeon in the form of a record or an alarm.

A voltage detected by electrode 16A at left laryngeal muscles 35 is amplified by the processing circuit at 57. The voltage reading at a tissue site is dependent on a number of factors. Changes in voltage can be caused by electrical stimulation to the nerve controlling that tissue site or by contact or manipulation of that nerve. A reference electrode 55 (not depicted in FIGS. 1-6) is attached to a reference site 56 on the patient's body (e.g. the chest, arms or legs). It is desirable to have a reference electrode 55 to screen out electrical impulses, from outside sources, which can be detected throughout a patient's body. The voltage detected at the reference site is amplified by the processing device at an amplification device 58. The two amplified signals from 57 and 58 are then compared at a comparison device 60 and any difference in those signals is stored at 62. The second electrode in the electrode pair, electrode 16B, also receives a voltage from left laryngeal muscles 35, which is transmitted to the processing machine, which amplifies the voltage at an amplification device 59 and compares it with the signal from reference electrode 55 at a comparison device 61. Any difference in those voltages is stored at 63. Signals from storage 62 and storage 63 are then compared at a comparison device 64.

The signals from comparison device 60 and comparison device 61 each represent the difference in voltage between laryngeal muscles 35 and reference site 56. The signals from comparison device 60 and comparison device 61 will be slightly different since the voltage reading at each point in left laryngeal muscles 35 will be slightly different. Any similarities between the signal from comparison device 60 and the signal from comparison device 61 will have been caused by voltage at reference site 56. Any difference in voltage will be registered at comparison device 64, and this will be the result of an EMG signal in the laryngeal nerve. The signal from comparison device 64 can then be displayed at a display device 65 or recorded at a recording device 66 in a conventional manner in order to provide a surgeon with information on EMG activity in the laryngeal muscle.

Detection of EMG signals in right laryngeal muscles 36 would be similarly carried out using electrode wires 16C and 16D.

A monopolar electrode works in a manner similar to a bipolar pair. Only a comparison at 60 would be made, however. Thus a monopolar electrode may result in EMG signals whose source is the reference site rather than a laryngeal muscle.

In order to monitor the EMG activity in both the right and left sets of laryngeal muscles, the electrode or electrode pair on each side of the endotracheal tube must be connected to a separate channel of an EMG processing machine. Thus, a device built according to the teachings of the present invention can be used to monitor both laryngeal nerves without having to adjust the endotracheal tube.

Electrode endotracheal tube 10 can be used to provide information on whether the tube has been properly placed within trachea 34. If the second wire portion 43 is not in contact with left laryngeal muscles 35, the electrode wires 16A and B will not be able to detect EMG signals within these muscles. One way of determining whether electrode endotracheal tube 10 is properly placed is by making use of the normal EMG signals from the laryngeal muscles associated with breathing. When a patient is under a light level of anesthesia, which conventionally occurs just before and shortly after the surgical procedure, these normal signals can still be detected in the laryngeal muscles. If the normal signals are not detected, it is an indication that the tube is not properly placed. Once the tube has been properly placed, the patient can be put under a deeper level of anesthesia. Under this deeper level, the normal EMG signals will cease, so that any EMG signal detected by the electrode endotracheal tube will have been caused by stimulation of a laryngeal nerve.

The electrode endotracheal tube can also be used to determine whether the laryngeal muscles are functioning properly prior to extubation or removal of the endotracheal tube. This is important because, if the laryngeal muscles are not functioning after a patient is extubated, breathing can be disrupted.

As previously discussed, damage to a laryngeal nerves can cause paralysis of the related laryngeal muscles, but paralysis can also be caused by damage inflicted to the laryngeal muscles upon intubation or by damage to that part of the brain which controls the laryngeal muscles. When patients are extubated, they are usually under a light level of anesthesia, thus the normal EMG signals associated with breathing can be detected in the laryngeal muscles. If these normal signals cannot be detected, the doctors can be prepared to take remedial measures when the tube is removed.

The foregoing detailed description has been given for clearness of understanding only and no unnecessary limitations should be understood therefrom, as modifications will be obvious to those skilled in the art.

What is claimed is:

1. An apparatus for monitoring the EMG signals of the laryngeal muscles, said apparatus comprising:
   an endotracheal tube formed from a flexible, nonelectrically conducting material and having a distal end, a proximal end, an exterior surface and a central axis;
   at least one electrode wire composed of electrically conducting material running in a direction parallel to said central axis at a location between said distal end and said proximal end;
   said electrode wire having an electrically insulated first wire portion located between said ends and an electrically uninsulated second wire portion, located between said first wire portion and said distal end, on the exterior surface of said endotracheal tube;
   said second wire portion comprising means for contacting said laryngeal muscles when said endotracheal tube is placed in the trachea for ventilation; and
   electrical connecting means for attaching said electrode wire to a machine which processes EMG signals.

2. The apparatus of claim 1 wherein said endotracheal tube comprises:
   an inflatable cuff located between said distal end and said second wire portion;
   a lumen, running in a direction parallel to said central axis;
   means, near said proximal end, for attaching said endotracheal tube to a source of compressed air;
   said lumen comprising means for communicating said cuff with said means for attaching said endotracheal tube to a source of compressed air.

3. The apparatus of claim 1 wherein:
   said endotracheal tube has a wall;
   said first wire portion is embedded within said wall of said endotracheal tube, and said second wire portion is unembedded relative to said wall.

4. The apparatus of claim 1 wherein:
   said second wire portion is positioned between a first location on said tube about 8 to 12 cm from said distal end and a second location on said tube 2 to 4 cm closer to said proximal end.

5. The apparatus of claim 1 wherein:
   said second wire portion is positioned between a first location on said tube about 10 cm from said distal end and a second location on said tube about 3 cm closer to said proximal end.

6. The apparatus of claim 1 wherein said endotracheal tube has a right side and a left side, and said apparatus further comprises:
   four of said electrode wires;
   two of said electrode wires forming a first bipolar electrode pair running along the right side of said endotracheal tube and comprising means for contacting the right laryngeal muscles when said endotracheal tube is properly inserted; and
   two of said electrode wires forming a second bipolar electrode pair running along the left side of said tube parallel to said first bipolar electrode pair and comprising means for contacting the left laryngeal muscle when said endotracheal tube is properly inserted.

7. A method of detecting EMG signals in laryngeal muscles, said method comprising the steps of:
   providing an endotracheal tube formed from flexible, non-electrically conducting material and having a distal end, a proximal end, an exterior surface and a central axis, said tube having at least one electrode wire of electrically conducting material running in a direction parallel to said central axis at a location between said distal end and said proximal end, said electrode wire having an electrically insulated first portion located between said ends and an electrically uninsulated second portion located between said first wire portion and said distal end of the exterior surface of said endotracheal tube;

placing said endotracheal tube in the trachea for ventilation;

contacting a set of laryngeal muscles with said second wire portion when said endotracheal tube is placed in the trachea for ventilation;

providing a device which processes EMG signals;

connecting said electrode wire to said processing device;

and stimulating the laryngeal nerve related to said set of laryngeal muscles.

* * * * *